United States Patent
Brenzel et al.

(10) Patent No.: US 8,920,434 B2
(45) Date of Patent: Dec. 30, 2014

(54) REMOTE BODY TISSUE ENGAGING METHODS AND APPARATUS

(75) Inventors: Michael P Brenzel, St. Paul, MN (US); Theodore P Dale, Minneapolis, MN (US); David M Costello, Waconia, MN (US); Paul J Hindrichs, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1180 days.

(21) Appl. No.: 11/361,193

(22) Filed: Feb. 23, 2006

(65) Prior Publication Data
US 2006/0200197 A1 Sep. 7, 2006

Related U.S. Application Data

(60) Provisional application No. 60/658,291, filed on Mar. 2, 2005.

(51) Int. Cl.
*A61B 17/08* (2006.01)
*A61B 17/32* (2006.01)
*A61B 17/34* (2006.01)
*A61B 17/00* (2006.01)

(52) U.S. Cl.
CPC . *A61B 17/3403* (2013.01); *A61B 2017/320052* (2013.01); *A61B 2017/3488* (2013.01); *A61B 2017/3482* (2013.01); *A61B 2017/00243* (2013.01); *A61B 2017/3484* (2013.01); *A61B 2017/00592* (2013.01); *A61B 2017/00623* (2013.01); *A61B 2017/00575* (2013.01); *A61B 2017/0061* (2013.01); *A61B 17/0057* (2013.01)
USPC ............................ 606/139; 606/151; 606/213

(58) Field of Classification Search
CPC ............. A61B 17/0482; A61B 17/062; A61B 17/0625; A61B 2017/00353; A61B 2017/2927; A61B 2019/2292
USPC .......... 606/151, 213, 139, 142, 158; 24/67.9, 24/546–547; 227/175.1
See application file for complete search history.

(56) References Cited

U.S. PATENT DOCUMENTS 4,458,386 A * 7/1984 Fernandez ...................... 24/67.9
5,008,982 A * 4/1991 Tsukamoto ..................... 24/67.9
(Continued)

FOREIGN PATENT DOCUMENTS

JP 06189971 A 7/1994
JP 2005521447 A 7/2005
(Continued)

OTHER PUBLICATIONS

Office Action from Japanese Application No. 2007-558135, dated Aug. 17, 2011.

*Primary Examiner* — Mark Mashack
(74) *Attorney, Agent, or Firm* — Lerner, David, Littenberg, Krumholz & Mentlik, LLP

(57) ABSTRACT

Apparatus is provided that can be delivered through a catheter to a remote location in a patient's body. The apparatus may include a first structure that can be positioned in all dimensions in a controlled manner and stabilized in that desired position, a second structure that can then position a lumen axis at a desired angle relative to the first structure, and a third member that can pass through the lumen and approach and engage with force (e.g., penetrate) a desired location on the anatomy without compromising maintaining the desired position. The apparatus effectively separates the forces needed for positioning and the forces needed for tissue engagement (e.g., penetration).

11 Claims, 6 Drawing Sheets

(56) References Cited

U.S. PATENT DOCUMENTS

| | | | |
|---|---|---|---|
| 5,171,233 A | 12/1992 | Amplatz et al. | |
| 5,406,680 A * | 4/1995 | Silverberg | 24/67.9 |
| 5,451,235 A * | 9/1995 | Lock et al. | 606/213 |
| 5,702,421 A * | 12/1997 | Schneidt | 606/213 |
| 5,797,960 A | 8/1998 | Stevens et al. | |
| 5,823,956 A | 10/1998 | Roth et al. | |
| 5,829,447 A | 11/1998 | Stevens et al. | |
| 5,855,614 A | 1/1999 | Stevens et al. | |
| 5,924,424 A | 7/1999 | Stevens et al. | |
| 6,079,414 A | 6/2000 | Roth et al. | |
| 6,152,144 A | 11/2000 | Van Der Burg et al. | |
| 6,234,177 B1 * | 5/2001 | Barsch | 128/897 |
| 6,290,674 B1 | 9/2001 | Roue et al. | |
| 6,346,074 B1 | 2/2002 | Roth et al. | |
| 6,401,720 B1 | 6/2002 | Stevens et al. | |
| 6,419,669 B1 | 7/2002 | Frazier et al. | |
| 6,436,088 B2 | 8/2002 | Frazier et al. | |
| 6,458,100 B2 | 10/2002 | Roue et al. | |
| 6,537,300 B2 | 3/2003 | Girton | |
| 6,562,052 B2 | 5/2003 | Nobles et al. | |
| 6,641,557 B1 | 11/2003 | Frazier | |
| 6,651,672 B2 | 11/2003 | Roth | |
| 6,679,268 B2 | 1/2004 | Stevens et al. | |
| 6,702,835 B2 | 3/2004 | Ginn et al. | |
| 6,776,784 B2 * | 8/2004 | Ginn | 606/151 |
| 7,727,245 B2 * | 6/2010 | Bender et al. | 606/139 |
| 2001/0041914 A1 | 11/2001 | Frazier et al. | |
| 2002/0099389 A1 | 7/2002 | Michler et al. | |
| 2002/0188318 A1 | 12/2002 | Aldrich et al. | |
| 2003/0028218 A1 | 2/2003 | Bauer | |
| 2003/0045893 A1 * | 3/2003 | Ginn | 606/151 |
| 2003/0069593 A1 | 4/2003 | Tremulis et al. | |
| 2003/0144694 A1 * | 7/2003 | Chanduszko et al. | 606/213 |
| 2003/0171774 A1 * | 9/2003 | Freudenthal et al. | 606/213 |
| 2003/0187467 A1 | 10/2003 | Schreck | |
| 2003/0208232 A1 | 11/2003 | Blaeser et al. | |
| 2003/0225421 A1 * | 12/2003 | Peavey et al. | 606/151 |
| 2004/0049211 A1 | 3/2004 | Tremulis et al. | |
| 2004/0176788 A1 | 9/2004 | Opolski | |
| 2004/0193147 A1 | 9/2004 | Malecki et al. | |
| 2004/0267191 A1 * | 12/2004 | Gifford et al. | 604/22 |
| 2005/0075665 A1 * | 4/2005 | Brenzel et al. | 606/213 |
| 2005/0251201 A1 * | 11/2005 | Roue et al. | 606/213 |
| 2005/0267495 A1 * | 12/2005 | Ginn et al. | 606/151 |
| 2005/0273119 A1 * | 12/2005 | Widomski et al. | 606/151 |

FOREIGN PATENT DOCUMENTS

| | | | | |
|---|---|---|---|---|
| JP | 2005525837 A | 9/2005 | | |
| JP | 2006230801 A | 9/2006 | | |
| JP | 2007519498 A | 7/2007 | | |
| WO | WO 98/07375 A1 | 2/1998 | | |
| WO | 0126542 A1 | 4/2001 | | |
| WO | WO 01/26542 A1 | 4/2001 | | |
| WO | WO 02/096295 A1 | 12/2002 | | |
| WO | WO 03/022159 A1 | 3/2003 | | |
| WO | WO 03/022160 A1 | 3/2003 | | |
| WO | WO 03/059152 A2 | 7/2003 | | |
| WO | WO 03/059152 A3 | 7/2003 | | |
| WO | WO 03/082076 A2 | 10/2003 | | |
| WO | WO 03/082076 A3 | 10/2003 | | |
| WO | WO 03/094742 A1 | 11/2003 | | |
| WO | WO 03/103476 A2 | 12/2003 | | |
| WO | WO 03/103476 A3 | 12/2003 | | |
| WO | WO 2004/012600 A2 | 2/2004 | | |
| WO | WO 2004012600 A2 * | 2/2004 | | A61B 10/00 |
| WO | 2004087235 A2 | 10/2004 | | |

* cited by examiner

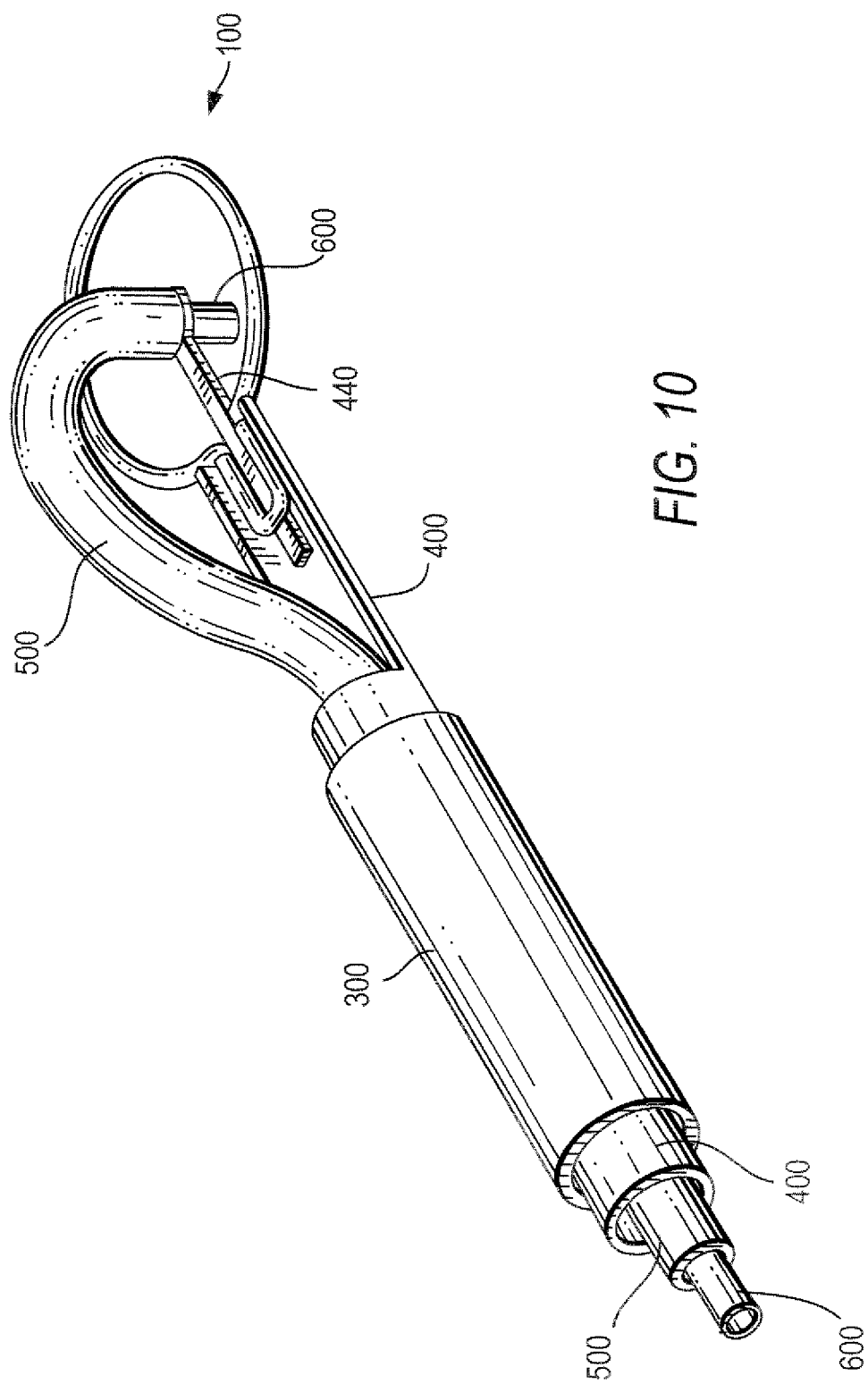

REMOTE BODY TISSUE ENGAGING METHODS AND APPARATUS

This invention claims the benefit of U.S. provisional patent application No. 60/658,291, filed Mar. 2, 2005, which is hereby incorporated by reference herein in its entirety.

BACKGROUND OF THE INVENTION

This invention relates to medical procedures and apparatus, and more particularly to medical procedures and apparatus that employ catheters to reach remote locations in a patient's body.

Certain catheter-based medical procedures may benefit from first establishing reference point apparatus at a remote location in the patient's body. Then an actual procedure can be performed in relation to the reference point apparatus. Examples of what is being referred to are procedures that involve crossing the atrial septum by piercing the septum from the right atrium to the left atrium such as in an ablation procedure, closing a patent foramen ovale ("PFO"), and any other left atrial procedure. If this could be done starting from stable and secure reference apparatus already in place at a desired location in the right atrium, the penetration of the septum could be made more precise, safer, and easier. It is therefore an object of this invention to provide such reference apparatus that can be delivered and deployed via a catheter, and which then provides a stable and secure "platform" from which one or more further procedures can be carried out.

SUMMARY OF THE INVENTION

Catheter delivered apparatus in accordance with the invention includes a first structure that can be positioned in all three dimensions in a controlled manner at a remote location inside a patient's body and stabilized in that desired position. The apparatus may further include a second structure that can then position a lumen axis at a desired angle relative to the first structure. A third structure may then pass through the second structure and approach and engage with force the desired location without compromising maintaining that location. The apparatus may thus effectively separate the forces needed for positioning from the forces needed for tissue engagement (e.g., penetration), thereby providing a safer and more controlled engagement (e.g., penetration) of the tissue.

In another aspect of the invention, catheter delivered apparatus in accordance with the invention includes a first expandable structure that can be positioned on one side of a tissue structure edge and a second expandable structure that can be positioned on the other side of the tissue structure edge, the first and second expandable structures being resiliently biased to diverge from one another so as to receive and engage the tissue structure edge between the first and second structures. At least the first structure includes at least two dimensions when expanded. The divergence of the second structure from the first structure involves use of a third dimension relative to the two previously mentioned dimensions. The first and second structures are preferably resiliently biased to expand, and are resiliently collapsible to approximately one dimension for delivery and removal via a catheter.

An illustrative use of the apparatus is in relation to a patient's PFO. One of the first and second structures can be deployed on one side of the limbus of the septum secundum (the upper portion of the septum between the left atrium and the right atrium of the heart). The other of the first and second structures can be deployed on the other side of the limbus. The structure on the PFO tunnel side of the limbus may enter and be self-centering in that tunnel. By engaging the limbus in this way, the engaging apparatus is prevented from being pushed farther into the heart. It is also located at a particular site in the heart and it is very stable at that location. For example, by straddling the limbus, by entering the PFO tunnel, and by including at least one structure that includes two dimensions substantially parallel to an adjacent tissue surface, the distal end of the apparatus is substantially prevented from rotating. This stable apparatus can be used as a "platform" for guiding other apparatus to a particular location and along a particular axis in the heart.

Further features of the invention, its nature and various advantages, will be more apparent from the accompanying drawings and the following detailed description.

BRIEF DESCRIPTION OF THE DRAWINGS

FIG. 10 is a simplified isometric view of another illustrative embodiment of apparatus in accordance with the invention.

DETAILED DESCRIPTION

Although the invention has other uses and can be modified in various respects for at least some of those other uses, the invention will first be described in the context of its application to transeptal punctures in patients with and without a patent foramen ovale ("PFO"). Later in this specification examples of other uses and possible modifications will be discussed.

Figure 2:
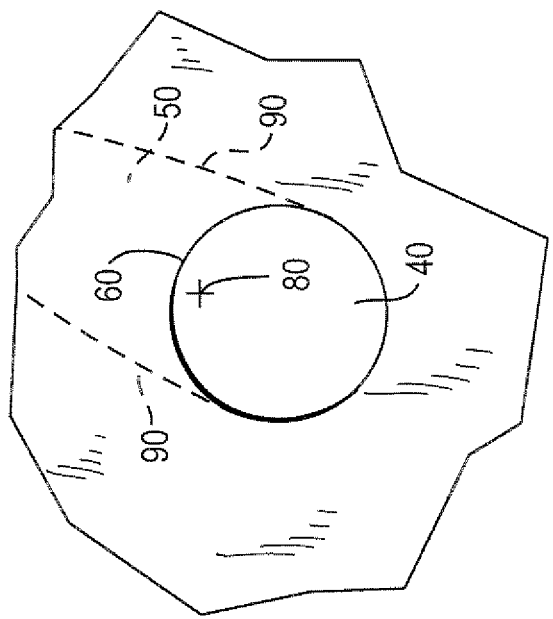
FIG. 2 is a view taken along the line 2-2 in FIG. 1.
Figure 1:
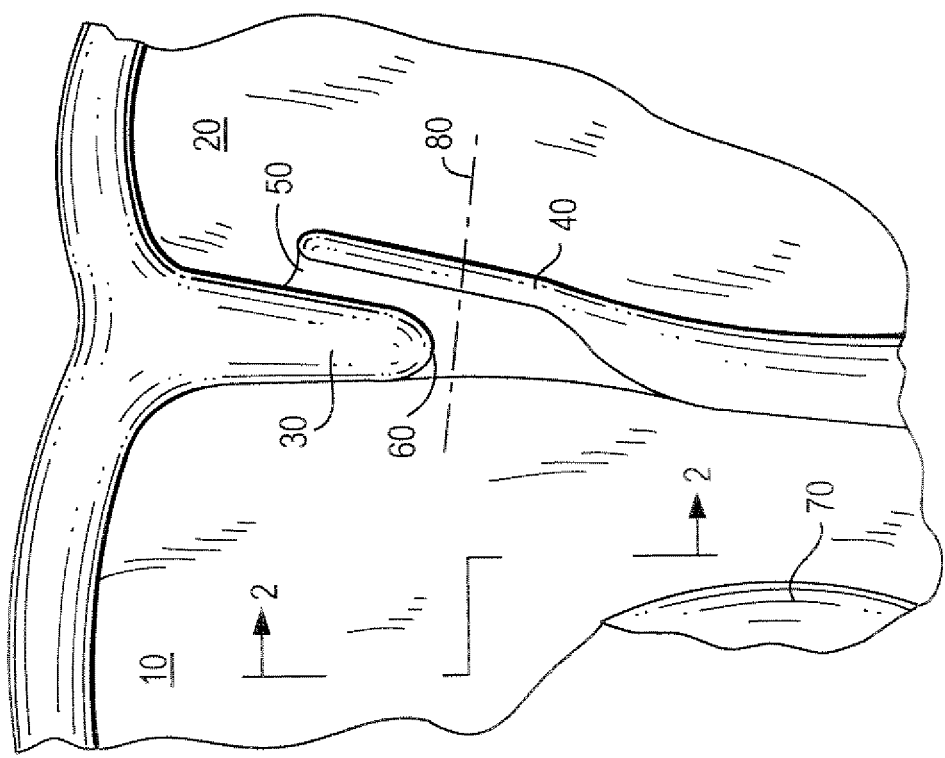
FIG. 1 is a simplified sectional view of a portion of a patient's anatomy.

The structure (anatomy) of a typical PFO is shown in FIGS. 1 and 2. The features shown in these FIGS. are as follows: right atrium 10, left atrium 20, septum secundum 30, septum primum 40, PFO 50 (a passageway through the septum between the left and right atria that is somewhat like a pocket with no bottom), limbus 60 of the septum secundum, wall 70 of the inferior vena cava, and edges 90 of the PFO tunnel where the primum and secumdum join (although in a PFO the primum and secundum do not join at the upper end of that tunnel). Also shown in FIGS. 1 and 2 is an axis and location 80 that are often regarded as particularly desirable for a transeptal puncture. The present invention provides instrumentation for facilitating such a transeptal puncture (although it will also be explained how the invention can alternatively facilitate puncture elsewhere).

Figure 4:
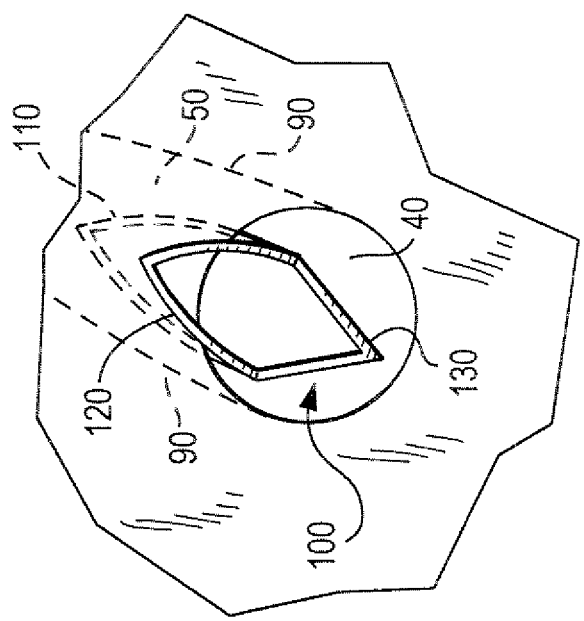
FIG. 4 is a view taken along the line 4-4 in FIG. 3.
Figure 3:
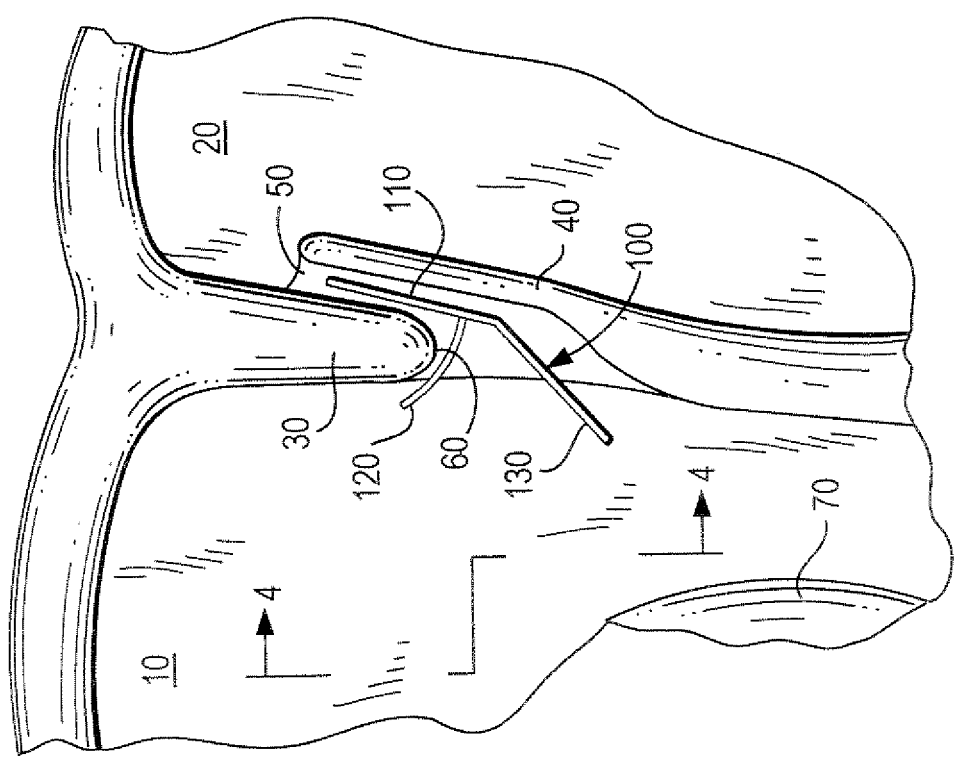
FIG. 3 is a view similar to FIG. 1 showing a portion of an illustrative embodiment of apparatus in accordance with the invention.

FIGS. 3 and 4 show an illustrative embodiment of a portion of apparatus in accordance with the invention, which apparatus has been positioned in relation to the PFO also in accordance with the invention. It is emphasized that FIGS. 3 and 4 show only a portion of the apparatus. In actual practice the components shown in FIGS. 3 and 4 would not be separated from other components and would not be in the patient unconnected to other components. But for clarity of initial depiction and explanation, it is helpful to first show these apparatus components in isolation.

The apparatus components shown in FIGS. 3 and 4 can be metal, wire-like components (e.g., of a highly elastic material such as nitinol). These apparatus components may be described as including three V-shaped parts 110, 120, and 130. V-shaped part 110 is partly positioned in the PFO tunnel 50. The apex of V 110 extends the greatest distance into the PFO tunnel. The spaced ends of V 110 may be just outside the PFO tunnel (i.e., still in right atrium 10).

Both of Vs 120 and 130 are in the right atrium. The spaced ends of V 120 are connected to or near the spaced ends of V 110. V 120 is resiliently biased to have the plane in which it lies diverge from the plane in which V 110 lies. This divergence causes V 120 to lie on the opposite side of septum secundum 30 from the side of that tissue structure on which V 110 lies. In other words, whereas V 110 is mostly in PFO tunnel 50 on one side of secundum 30, V 120 is in right atrium 10 on the other side of secundum. The planes in which Vs 110 and 120 lie form a V-shaped trough (FIG. 3) in which the limbus 60 of septum secumdum 30 lies.

The spaced ends of V 130 are connected to or near the spaced ends of Vs 110 and 120. Whereas the apexes of Vs 110 and 120 point generally upward in the heart, the apex of V 130 points generally down (toward the inferior vena cava, represented in part by wall 70).

Vs 110, 120, and 130 may be referred to collectively as structure 100.

Note that V 110 generally centers structure 100 in PFO tunnel 50 (i.e., between the edges 90 of the PFO tunnel). Vs 110 and 120 cooperate to stop upward movement of structure 100 when the trough between the planes of those two Vs reaches limbus 60. The relatively wide spacing between the free ends of all of Vs 110, 120, and 130, and the engagement of various portions of the Vs with adjacent tissue surfaces, tends to prevent structure 100 from rotating about an axis such as one that passes through the apexes of Vs 110 and 130. In other words, V 110 (for example) tends to remain relatively flat against the surface of septum primum 40.

Structure 100 is resiliently laterally collapsible. By this it is meant that the spaced apart ends of each of Vs 110, 120, and 130 can be collapsed together (thereby substantially closing each of the Vs from two dimensions to one dimension). In addition, Vs 110 and 120 are resiliently collapsible toward one another (i.e., so that they are nearly in the same plane or, if Vs 110 and 120 are each also collapsed, then they are both nearly on the same line). V 130 is also resiliently deflectable into alignment with the other fully collapsed and aligned Vs, although the components of V 130 continue to extend away from the components of the other Vs.

Figure 6:
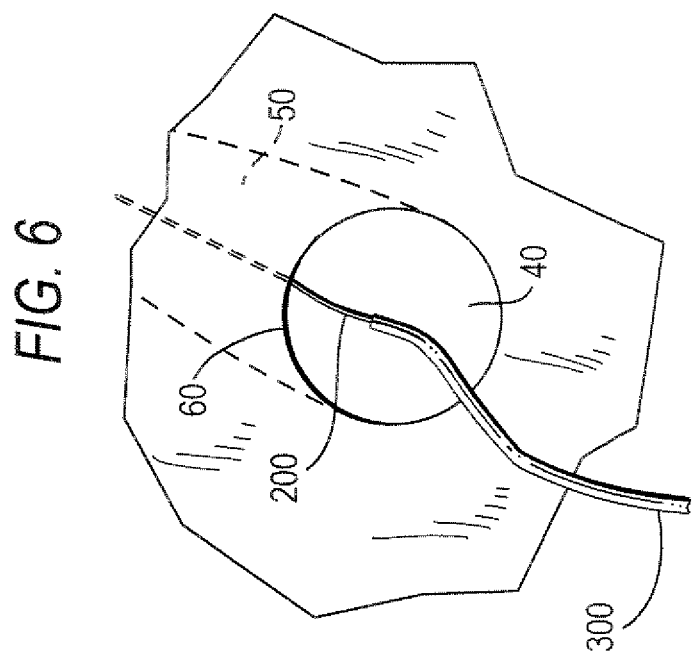
FIG. 6 is a view taken along the line 6-6 in FIG. 5.
Figure 5:
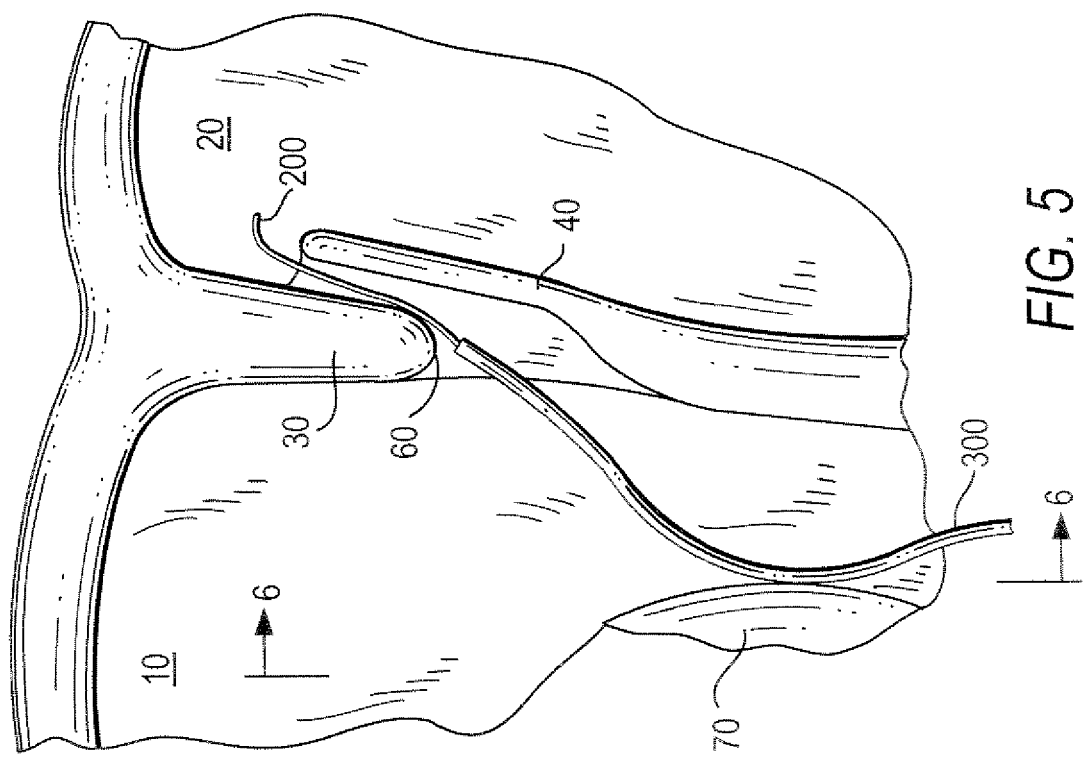
FIG. 5 is another view similar to FIG. 1 showing a portion of an illustrative embodiment of other apparatus in accordance with the invention.

In the collapsed and aligned condition described in the preceding paragraph, structure 100 can be delivered percutaneously into the patient's heart via a catheter. For example, FIGS. 5 and 6 show catheter apparatus 300 that may be used to deliver structure 100 (and related components) to the site shown in FIGS. 3 and 4. Catheter 300 reaches the patient's heart via the patient's circulatory system, leading ultimately to the inferior vena cava. The distal portion of catheter 300 is resiliently shaped (as generally shown in FIGS. 5 and 6) to contact vena cava wall 70 and from that point to aim toward PFO 50. If desired, a guidewire 200 may be extended from the distal end of catheter 300 into and through PFO 50. Guidewire 200 can help to make sure that the distal end of catheter 300 remains properly positioned relative to the entrance to the PFO, and it can also serve as a rail alone which additional components can be pushed from the end of catheter 300 into the PFO. Although this is something of a simplification (to be more fully explained below), structure 100 can be pushed from the distal end of catheter 300, and when thus freed from constraint by the catheter, structure 100 resiliently expands to the condition shown in FIGS. 3 and 4. When structure 100 is no longer needed in the patient, it can be collapsed back into the catheter and withdrawn from the patient with or via the catheter.

Figure 7:
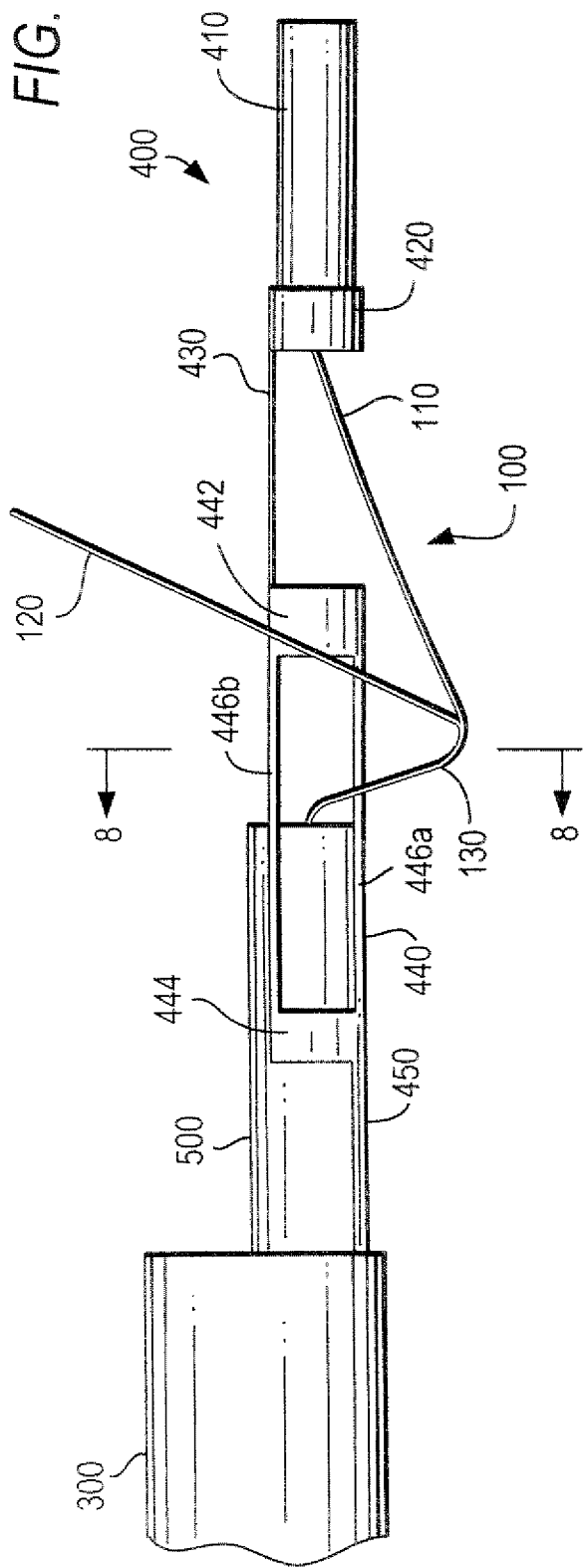
FIG. 7 is a simplified elevational view of an illustrative embodiment of a portion of illustrative apparatus in accordance with the invention.

FIG. 7 shows the components on which structure 100 is mounted in catheter 300 (although FIG. 7 shows the condition of the apparatus after these components and structure 100 have been pushed out of the distal end of the catheter). The components shown in FIG. 7 include distal tubular member 410, tubular member 420, linking member 430, guide structure 440, and proximal link member 450. These elements are all rigidly secured to one another, and they may sometimes be referred to collectively as assembly 400. Associated with these elements (but movable relative to them) is delivery tube 500.

Tube 410 may be made of a relatively soft and flexible plastic material in order to make the distal end of assembly relatively atraumatic. Guide wire 200 (FIGS. 5 and 6) may pass through tube 410 (or tube 410 may itself perform a function like a guide wire by being an early entrant into PFO tunnel 50 in the manner shown for guide wire 200 in FIGS. 5 and 6). The remaining components 420, 430, 440, and 450 of assembly 400 are preferably made of metal.

The shape of guide structure 440 warrants the following further discussion. The distal-most portion 442 of structure 440 may be a tube. The proximal-most portion 444 of structure 440 may be U-shaped, open at the top as viewed in FIG. 7. The portion of structure 440 between elements 442 and 444 may comprise four strips 446a-d (see FIG. 8) that form an annular array around delivery tube 500.

The distal (apex) end of V 110 is attached to the side wall of tube 420. The arms of V 110 may not actually come together at the apex, but rather tube 420 may effectively provide the apex of that V. Thus the distal end of each arm of V 110 may be connected to a respective opposite side of the wall of tube 420, with that tube providing the apical connection between the arms.

Figure 8:
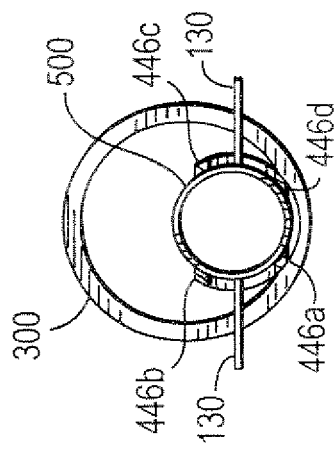
FIG. 8 is a simplified sectional view taken along the line 8-8 in FIG. 7.

The proximal (apex) end of V 130 may be similarly connected to the wall of delivery tube 500 (see again FIG. 8). Each arm of V 130 extends out of a respective opposite side of guide structure 440 between a respective pair of the strips 446 of that structure. For example, as viewed in FIG. 8, the left-hand arm of V 130 extends out between strips 446a and 446b, and the right-hand arm of V 130 extends out between strips 446c and 446d. As in the case of V 110, the arms of V 130 may not actually come together at the apex of that V, but instead the distal end of tube 500 may effectively form the apex of V 130.

V 120 straddles assembly 400. The apex of V 120 is toward the top as viewed in FIG. 7.

Assembly 400 is movable axially (longitudinally) relative to catheter 300. This allows assembly 400 to be extended from the distal end of catheter 300 or retracted into the catheter. Tube 500 is movable axially (longitudinally) relative to assembly 400 and catheter 300. For example, proximal retraction of tube 500 relative to assembly 400 from the position shown in FIG. 7 tends to straighten and collapse Vs 110 and 130. Collapsing Vs 110 and 130 also collapses V 120. Then further proximal retraction of tube 500 together with assembly 400 draws everything into the distal end of catheter 300. This folds already-collapsed V 120 down onto assembly 400 for entry into the distal end of the catheter. Reversing the above-described relative motions allows the structure to deploy (resiliently in the case of Vs 110, 120, and 130) to the condition shown in FIG. 7.

The condition of the apparatus shown in FIG. 7 corresponds to the condition of structure 100 in FIGS. 3 and 4, assuming that everything else in FIG. 7 has been positioned in the patient as shown in FIGS. 5 and 6. Thus, as described above in connection with FIGS. 3 and 4, deployed V 110 in FIG. 7 centers structure 100 in PFO tunnel 50; deployed V 120 in FIG. 8 cooperates with deployed V 110 to engage the limbus 60 of secundum 30 and thereby prevent further distal motion of both structure 100 and assembly 400 relative to limbus 60; and deployed Vs 110 and 120 cooperate with the adjacent tissue to prevent structure 100 and assembly 400 from rotating about a longitudinal axis of those components (i.e., a left-right axis in FIG. 7). Thus the features that have been described up to this point substantially fix components 100 and 400 in a very secure and stable way at a particular location relative to PFO 50.

Figure 9:
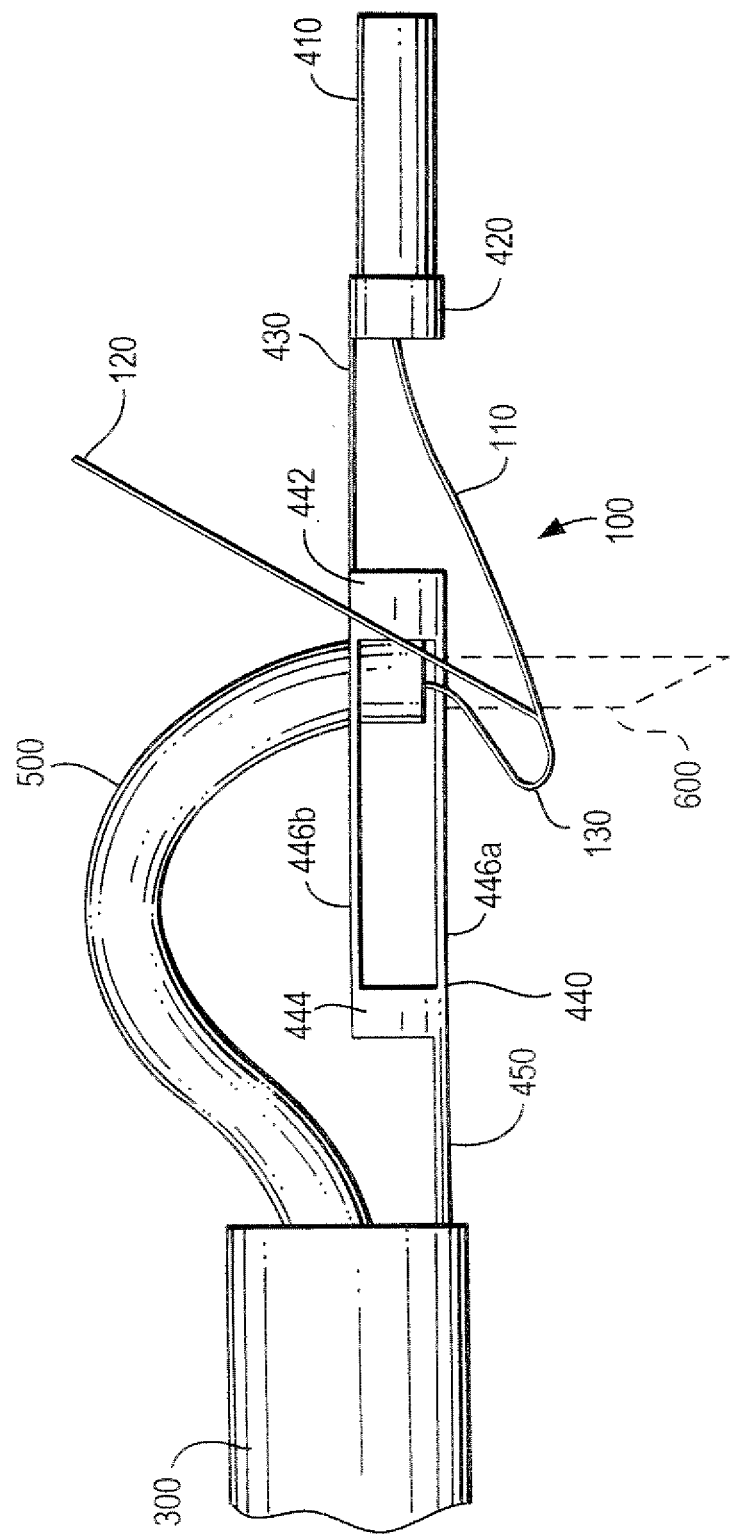
FIG. 9 is similar to FIG. 7 showing the apparatus in another operating conduction.

It is now meaningful to describe a possible further feature of the invention as follows. After the apparatus is in place in the patient as described above in connection with FIG. 7, tube 500 can be pushed farther in the distal direction relative to assembly 400. At first the distal portion of tube 500 remains straight. Eventually, however, the distal end of tube 500 contacts tube 442, which it cannot pass through. Further distally-directed pushing on tube 500 causes the distal portion of that tube to buckle as shown in FIG. 9. The extreme distal end of tube 500 cannot get away from assembly 400 because it is trapped by the arms of V 130 passing between strips 446a and *b* on one side and strips 446c and *d* on the other side. Also, just as the distal end of tube 500 is too large to pass through cylinder 442, it is also too large to pass between strips 446a and 446d. The distal portion of tube 500 can, however, buckle upwardly as viewed in FIG. 9 out of the top of structure 400. This is possible because component 444 has a U shape that is open at the top, and because the space between strips 446b and 446c is great enough to permit tube 500 to deflect upwardly out of structure 400. Thus it will be seen that structure 400 causes the distal portion of tube 500 to buckle, but only permits buckling in one direction, i.e., upwardly as viewed in FIG. 9.

It will be noted that V 130 changes shape somewhat during the above-described further distal motion and buckling of tube 500, but this does not significantly alter the disposition of Vs 110 and 120. Thus Vs 110 and 120 continue to hold the distal portion of the apparatus at the previously described location in the patient and with the previously described orientation relative to the patient's tissue structure.

The result of the above-described constrained buckling of tube 500, together with the other constraints described above (i.e., Vs 110 and 120 substantially fixing the location and orientation of structure 400 relative to the patient's tissue structure), is that the distal end of tube 500 in FIG. 9 is substantially perpendicular to septum primum 40 like axis 80 in FIGS. 1 and 2. The distal end of tube 500 is also at the location shown for axis 80 in FIGS. 1 and 2. Tube 500 can therefore be advantageously used to guide tissue piercing apparatus to and through primum 50 at the location and in the direction of axis 80 in FIGS. 1 and 2. The continued presence of V 110 in PFO tunnel 50 helps to provide the apparatus with the reaction force that may be needed to get the tissue piercing structure through the primum. Such reaction force may also be provided by continued contact of catheter 300 with inferior vena cava wall 70. The piercing can be done in an extremely controlled way to ensure that the piercing instrument does not suddenly break through the primum and go too far across left atrium 20 to a point where it may cause undesirable damage to other tissue. (For completeness, a piercing structure 600 is shown in dotted lines in FIG. 9 extending distally from the distal end of structure 500.)

If it is desired to change the location relative to limbus 60 of the distal end of buckled tube 500, that can be done by shifting the proximal end of tube 442 to the left relative to the location shown in FIGS. 7 and 9. This is a design change, not an operational change, in embodiments of the type illustrated herein.

If the patient does not have a PFO, limbus 60 may still be an accessible feature of the patient's anatomy. To make use of that feature in much the same way as described above for PFOs, components 410, 420, 430, and 110 may be variously shortened or eliminated. The apparatus may then still be able to engage limbus 60 in somewhat like the fashion described above, with many of the attendant advantages described above. Thus use in connection with a PFO is only illustrative, and the invention may be alternatively used in connection with any other suitable tissue structures, with possible modifications of the apparatus that are appropriate for such other tissue structures.

FIG. 10 shows an alternative embodiment with many of the attributes that are described above but that may be usable with anatomies that are similar to or different from those shown as described above. Reference numbers that have been used above are used again in FIG. 10 for the same or generally similar components.

In FIG. 10, structure 400 is selectively extendable from catheter 300. Structure 400 carries resiliently expandable structure 100. When structures 100 and 400 are inside catheter 300, structure 100 is collapsed by the catheter. When structures 100 and 400 are extended from catheter 300 (as shown in FIG. 10), structure 100 resiliently expands to the relatively large two-dimensional shape shown in FIG. 10. This two-dimensional shape of structure 100 may be held relatively flat against an adjacent tissue surface (e.g., primum 40) by having the distal-most portion of structure 100 engaged under limbus 60 (even if the patient does not have a PFO) and/or by contact of catheter 300 with inferior vena cava wall 70. (A back side of deployed structure 500 bearing against an opposite tissue surface may later also help to hold structure 100 in the desired position against the adjacent tissue surface.) Pushing structure 100 against the underside of limbus 60 (even in the absence of a PFO) may also help to position the distal end of the apparatus both axially and laterally (i.e., side-to-side in the plane defined by deployed structure 100).

After structure 100 has been deployed as described above, structure 500 may be pushed distally relative to the other components. Structure 400 includes a component 440 that prevents the distal end of structure 500 from going beyond a desired point within deployed structure 100. Distal pushing of structure 400 therefore causes its distal portion to buckle as shown in FIG. 10. This aims the distal end of structure 400 toward a desired tissue location and with a desired angle relative to the surface of that tissue. Tissue engaging (e.g., penetrating) structure 600 can then be extended distally from structure 500 as shown in FIG. 10 to engage (e.g., penetrate) the tissue at the desired location and with the desired angle.

Deployment of the FIG. 10 apparatus is reversible. Structure 600 can be pulled back into structure 500. Structure 500 can be pulled back to straighten it. All of structures 100, 400, and 500 can be pulled back into catheter 300.

It will be noted that the apparatus of this invention can attain and maintain a desired position in a patient's anatomy without the necessity for tissue penetration. (Of course, tissue penetration may come later by other components such as 600.) Moreover, this can be done in a relatively open part of the anatomy such as the right atrium without filling that anatomy with any large structure and without interfering with continued normal functioning of the anatomy while the apparatus is present in the anatomy.

It will be understood that the foregoing is only illustrative of the principles of the invention, and that various modifications can be made by those skilled in the art without departing from the scope and spirit of the invention. For example, the materials that are mentioned above for certain components are only illustrative, and other suitable materials can be used instead if desired.

The invention claimed is:

1. Catheter-deliverable apparatus comprising:
a first expandable structure that can be positioned on a first side of a patient's body tissue structure edge; and
a second expandable structure that can be positioned on a second side of the patient's body tissue structure edge, wherein each of the first and second expandable structures are expandable from substantially one dimension to a two-dimensional configuration,
wherein the first expandable structure is a first V-shaped part having spaced ends, and the second expandable structure is a second V-shaped part having spaced ends, the spaced ends of the second V-shaped part being directly connected to the spaced ends of the first V-shaped part, and
wherein the first and second expandable structures are resiliently biased to diverge from one another so that, in use, the tissue structure edge can be received between the first and second expandable structures and a first plane in which the first V-shaped part lies and a second plane in which the second V-shaped part lies form a V-shaped trough; further comprising a third V-shaped part having spaced ends, the spaced ends of the third V-shaped part being directly connected to the spaced ends of each of the first and second V-shaped parts.

2. The apparatus defined in claim 1 wherein the first expandable structure is resiliently biased to expand.

3. The apparatus defined in claim 2 wherein the second expandable structure is resiliently biased to expand.

4. The apparatus defined in claim 1 wherein the resilient bias of the first and second expandable structures to diverge urges the two dimensions of the expanded first expandable structure to pivot away from the two dimensions of the expanded second expandable structure in a third dimension that is generally perpendicular to the two dimensions of at least one of the first and second expandable structures.

5. The apparatus defined in claim 4 wherein the resilient bias of the first and second expandable structures to diverge is reversible to facilitate withdrawal of the apparatus via the catheter.

6. The apparatus defined in claim 5 wherein expansion of the first and second expandable structures is reversible to facilitate withdrawal of the apparatus via the catheter.

7. The apparatus defined in claim 1 wherein the first expandable structure is adapted to be received in a patient's PFO tunnel in use.

8. The apparatus defined in claim 1 further comprising:
guide structure associated with the first and second expandable structures for use in guiding another structure to a particular location relative to the first and second expandable structures.

9. The apparatus defined in claim 8 wherein the guide structure is further adapted to permit the another structure to deflect in a particular plane relative to the first and second expandable structures.

10. The apparatus defined in claim 9 wherein the particular plane is substantially perpendicular to a plane in which the first expandable structure is disposed when expanded.

11. The apparatus defined in claim 10 wherein the guide structure is further adapted to hold a distal portion of the another structure at a particular location, while permitting a more proximal portion of the another structure to deflect in the particular plane.

* * * * *